United States Patent [19]

Scheiner et al.

[11] Patent Number: 5,366,493
[45] Date of Patent: Nov. 22, 1994

[54] DOUBLE HELIX FUNCTIONAL STIMULATION ELECTRODE

[75] Inventors: Avram Scheiner, University Heights; E. Byron Marsolais, Shaker Heights; J. Thomas Mortimer, Cleveland Heights; Thomas P. Kicher, South Euclid, all of Ohio

[73] Assignee: Case Western Reserve University, Cleveland, Ohio

[21] Appl. No.: 652,039

[22] Filed: Feb. 4, 1991

[51] Int. Cl.$^5$ .............................................. A61N 1/05
[52] U.S. Cl. .................................................... 607/116
[58] Field of Search ........ 128/783, 799, 899, 784–786, 128/419 P, 423 W, 642, 420.5; 607/48, 115, 116, 122, 128

[56] References Cited

U.S. PATENT DOCUMENTS

| | | | |
|---|---|---|---|
| 3,760,812 | 9/1973 | Timm et al. | 128/784 |
| 4,226,228 | 10/1980 | Shin et al. | |
| 4,282,885 | 8/1981 | Bisping . | |
| 4,321,931 | 3/1982 | Hon . | |
| 4,414,986 | 11/1983 | Dickhudt et al. | 128/785 |
| 4,590,946 | 5/1986 | Loeb . | |
| 4,640,983 | 2/1987 | Comte | 128/784 X |
| 4,662,382 | 5/1987 | Sluetz et al. | 128/419 P X |
| 4,716,888 | 1/1988 | Wesner | 128/785 |
| 4,832,051 | 5/1989 | Jarvik et al. . | |
| 4,840,186 | 6/1989 | Lekholm et al. . | |
| 4,964,414 | 10/1990 | Handa et al. | 128/642 X |
| 4,989,617 | 2/1991 | Memberg et al. | 128/642 X |
| 5,016,645 | 5/1991 | Williams et al. . | |

OTHER PUBLICATIONS

Functional Tasks Restored in Paralyzed Man Using Electronic Orthotics, by E. B. Marsolais, Rudi Kobetic and Howard J. Chizeck 1989.
Functional Electrical Stimulatior, Medical Equipment Designer Mar. 1990.
A Double Helix Electrode for Functional Electrical Stimulation, by Avram Scheiner and E. Byron Marsolais 1990.
Improved Voluntary Gait Pattern Post Stroke, Following Treatment With The Multi-Channel, Intramuscular, Microprocessor-Based FNS System, by Janis L. Jacobs, Katherine Barnicle and E. Byron Marsolais 1991.

Primary Examiner—Lee S. Cohen
Assistant Examiner—Samuel Gilbert
Attorney, Agent, or Firm—Calfee, Halter & Griswold

[57] ABSTRACT

First and second electrical wires (10), (12) are wrapped helically around a polyprolene core (22). Along a single helical portion (A), a sheath (24) is placed over the spiral wound wires and core. In an open double helix portion (B), the core with spiral wound wires is wrapped into an open helix. At an electrical stimulation portion (C), insulation is removed from the wires such that bare conductors (14), (16) are wrapped spirally around the core. The core with the spiral wrapped conductors is wrapped in an open helix. A plurality of barbs (32) are mechanically connected along the entire length of the exposed electrical conductor surface. The core extends beyond the end of the electrical conductor surface to facilitate insertion into a selected site with a cannula (64).

14 Claims, 5 Drawing Sheets

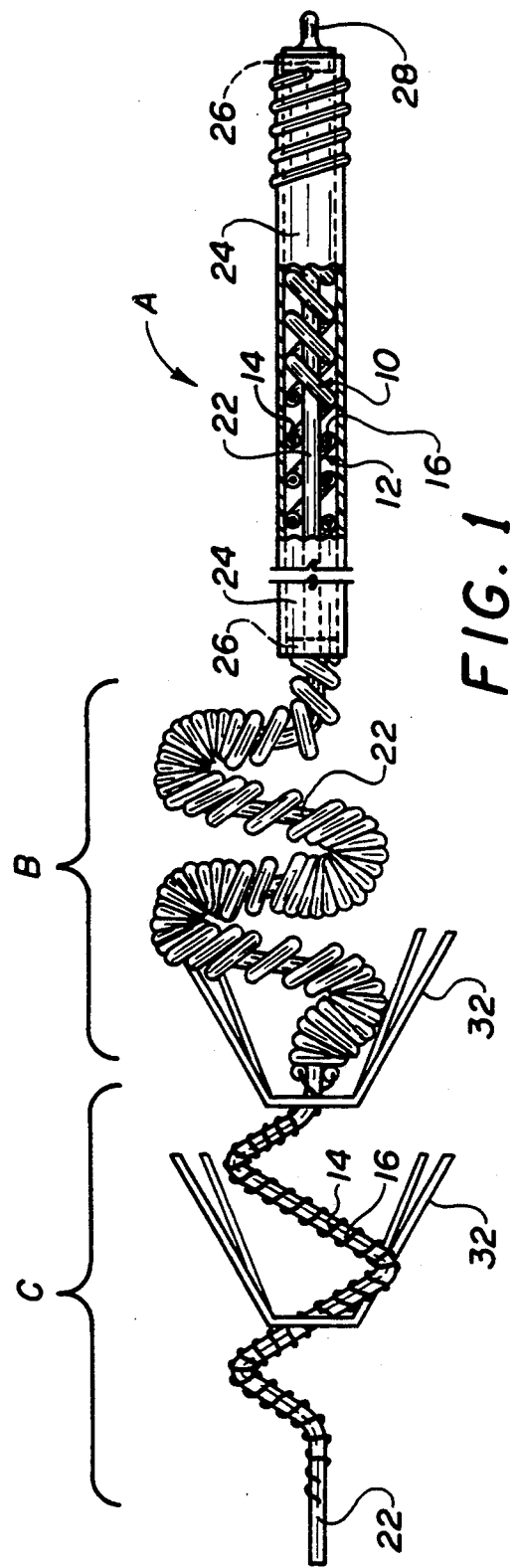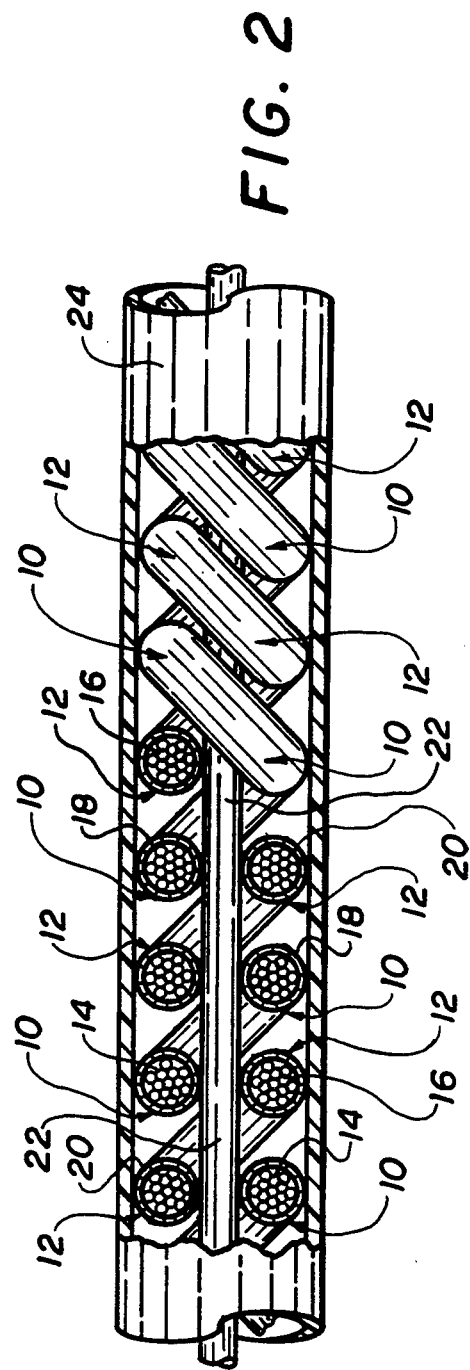

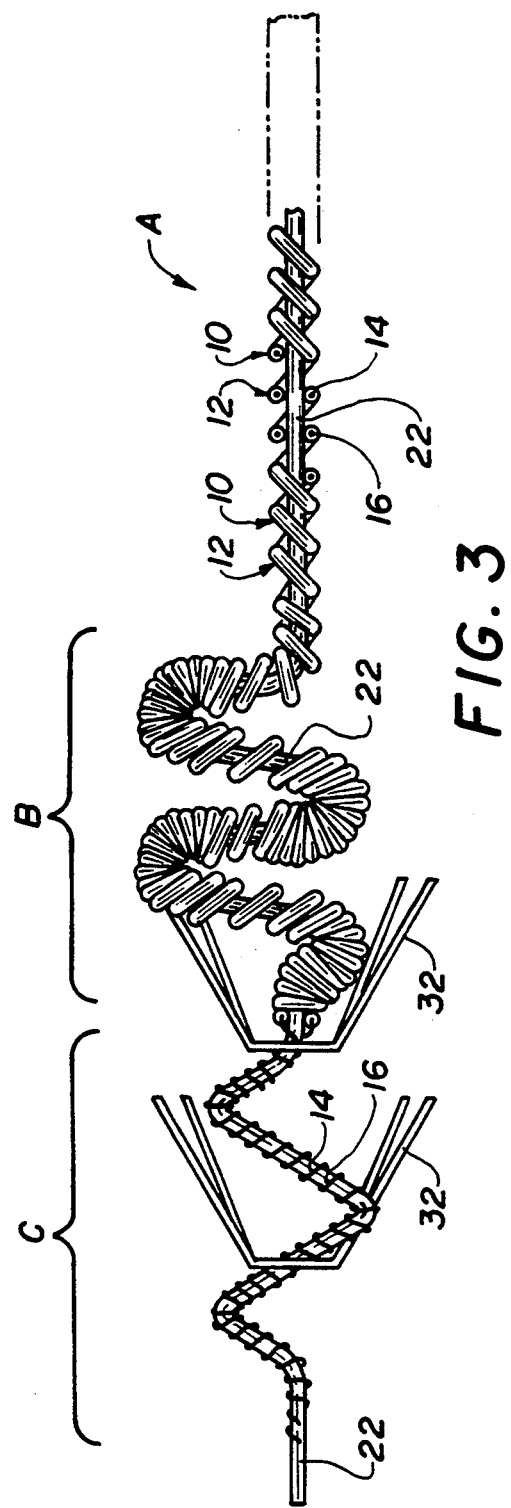
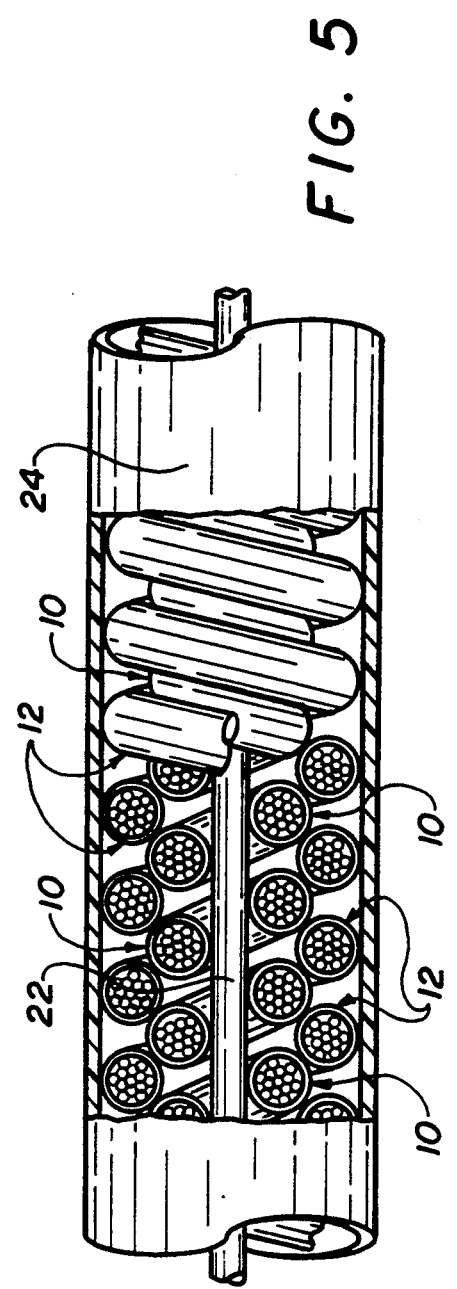

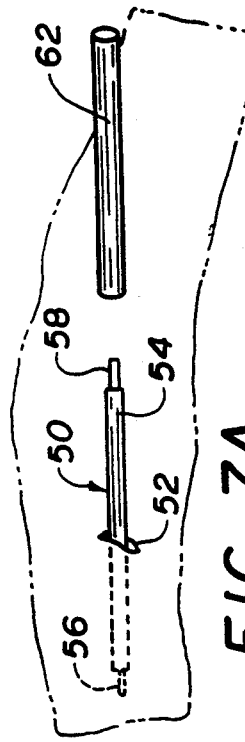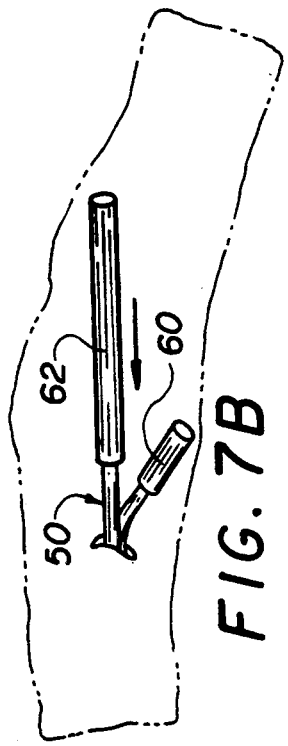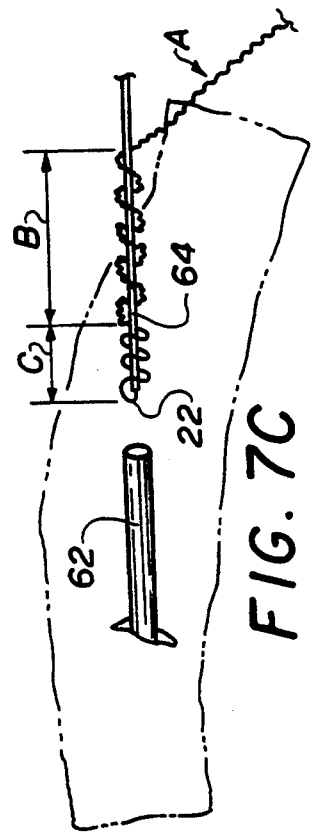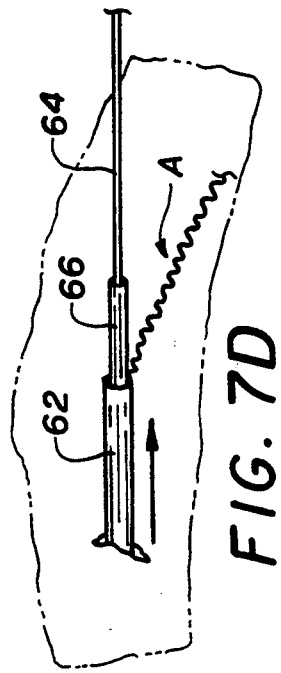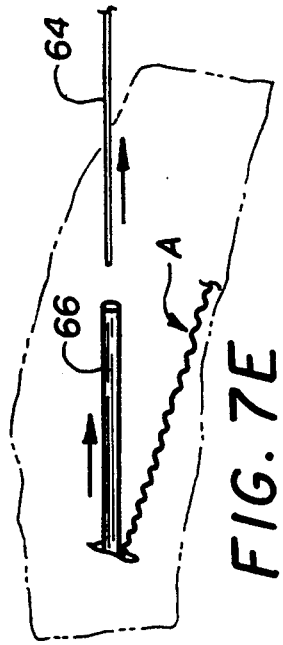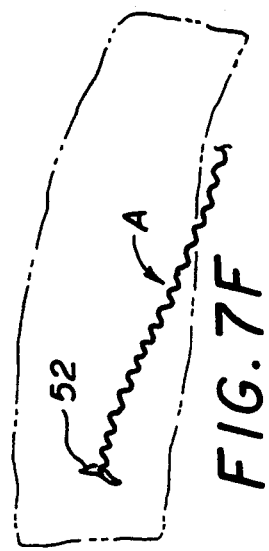

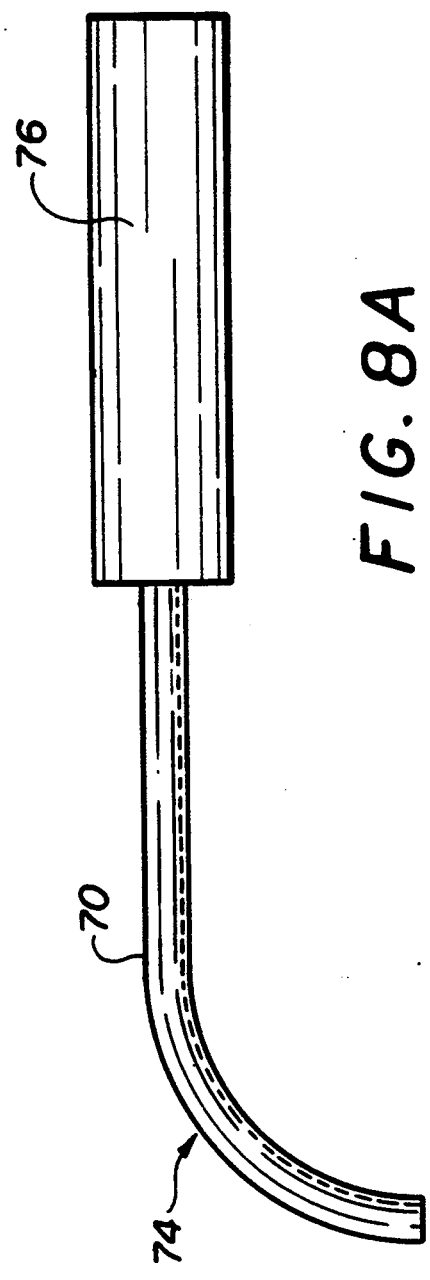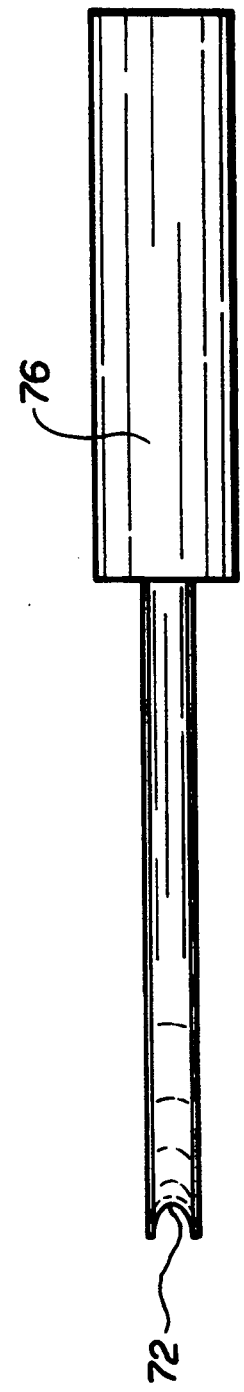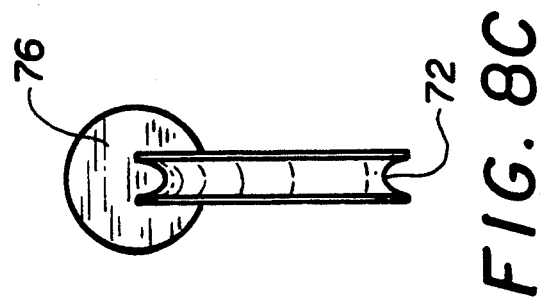

DOUBLE HELIX FUNCTIONAL STIMULATION ELECTRODE

BACKGROUND OF THE INVENTION

The present invention relates to the electrode art. It finds particular application in conjunction with electrodes for stimulating skeletal muscles and will be described with particular reference thereto.

Functional restoration of a paralyzed limb can be achieved through the application of technique known as functional electrical stimulation (FES). In this technique, an electrode is implanted at an appropriate point in one of the patients skeletal muscles. The electrode must be positioned accurately, generally with a tolerance of a couple of millimeters. Once the electrode is implanted, its lead wire is run under tile skin to an exit site or connected to an implanted stimulator or other similar device.

Physiological movements are relatively complex, frequently requiring the coordinated operation of numerous muscles. To achieve full functional control, a patient may need as many as 50 or more implanted electrodes. The leads from the plurality of electrodes run through the tissue and the muscles to an exit site or are connected to an implanted stimulator or other similar device.

The skeletal muscle tissue environment is much more severe than the environment for brain electrodes, skin surface electrodes, heart electrodes, or the like. The stimulated skeletal muscle is continually contracting and expanding. The implanted electrode moves a relatively large distance with each expansion and contraction relative to movement which brain, skin, or heart electrodes undergo. One problem with the prior art electrodes has been a loosening of the electrodes due to the muscle contraction and expansion. Another significant problem with the prior art electrodes has been failure of the electrode leads attributable in large part to the flexing and stress which they undergo during muscle contraction and expansion.

Once the electrodes are implanted and the leads are run under the skin, it is difficult to tell when a lead or electrode has failed. More specifically, electrical continuity of the lead is commonly checked by placing a current into the electrode lead at the interface and completing the circuit with an electrode on the surface of the patient's skin. The patient's muscle, skin, and other tissue between the surface electrode and the implanted electrode has a relatively high impedance. Frequently, it is difficult to distinguish between the high impedance attributable to an electrical break in the lead from the high impedance of the patient tissue.

The present invention contemplates a new electrode and lead combination which overcomes the above-referenced problems and others.

SUMMARY OF THE INVENTION

In accordance with the present invention, an FES electrode and lead are formed with a double helix lead. More specifically, the lead includes an insulated conductor which is wrapped spirally around a polymeric core. The polymeric core with spiral wrapped conductor is wrapped into an open helix. In this manner, an open helix configuration is defined which has a very low spring constant and provides excellent stress relief.

In accordance with another aspect of the present invention, an FES electrode with an elongated conductive surface is provided. A multiplicity of metallic barbs or anchors are connected at intervals along the elongated electrically conductive surface. By spacing the barbs, the loads on the electrode and the muscle tissue are distributed during muscle contraction.

In accordance with another aspect of the present invention, an FES electrode is interconnected with a dual lead wire. That is, two insulated lead wires are interconnected at the electrode. When the electrode is being utilized for electrical stimulation, both leads can be used in parallel for providing an electrical current path redundancy. When a question arises as to the integrity of the leads, the leads are operated in series such that a current passes in one lead to the electrode and back out the other lead providing a ready measure of lead impedance.

In accordance with another aspect of the present invention, an FES electrode is implanted with great precision and with minimal tissue damage. A needle-like probe with an insulated body is inserted through the skin to an implant site. Electrical current is passed through the probe and the muscular response is measured. The angle and depth of the probe is measured. A sheath is slipped over the probe to the appropriate depth and the probe removed. The electrode mounted on a cannula is inserted through the sheath to the implant site, after which the cannula and sheath are removed leaving the electrode implanted.

One advantage of the present invention resides in its durability and long useful life after implantation.

Another advantage of the present invention resides in its simplicity of implantation and positioning.

Another advantage of the present invention resides in its anchoring firmness and resistance to pull-out.

Still further advantages of the present invention will become apparent to those of ordinary skill in the art upon reading and understanding the following detailed description.

BRIEF DESCRIPTION OF THE DRAWINGS

The invention may take form in various parts and arrangements of parts and in various steps and arrangements of steps. The drawings are only for purposes of illustrating a preferred embodiment and are not to be construed as limiting the invention.

FIG. 1 illustrates a preferred embodiment of an electrode and lead construction in accordance with the present invention;

FIG. 2 is an enlarged side sectional view of a single helix lead portion of the electrode lead of FIG. 1;

FIG. 3 is an enlarged side sectional view of an alternate embodiment of the single helix lead portion without sheathing;

FIG. 5 is an enlarged side sectional view of an alternate embodiment of tile lead portion;

FIGS. 7A-7F are illustrative of the electrode implantation procedure; and

FIGS. 8A, 8B, and 8C are side, bottom, and front views, respectively, of a retractor used during the implantation procedure.

DETAILED DESCRIPTION OF THE PREFERRED EMBODIMENTS

Figure 4:
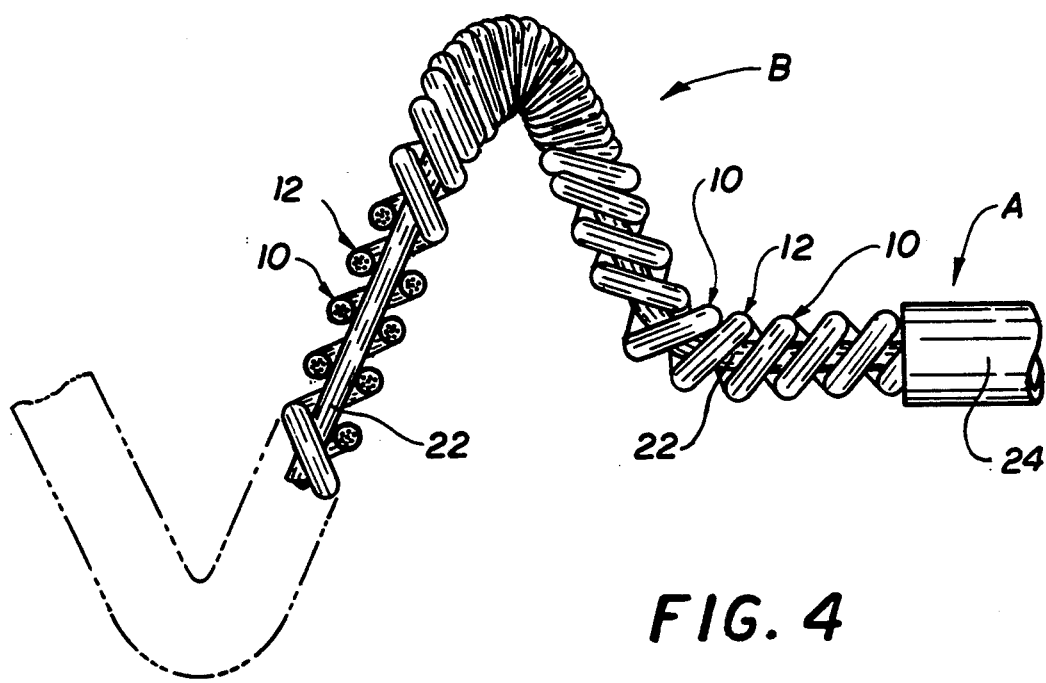
FIG. 4 is an enlarged side sectional view of the double helix portion of the electrode of FIG. 1.

With reference to FIG. 1, a single helix lead portion A extends from an electrical connection end to an open double helix lead portion B. The open double helix lead portion extends under the skin through regions which undergo significant elongation and contraction during muscular movement. The open double helix lead portion terminates at its opposite end with a double helix electrical contact portion C which is inserted into the muscle tissue at the implant site.

With continuing reference to FIG. 1, and further reference to FIG. 2, the single helix portion A includes two multi-strand wires 10, 12. The first and second multi-strand wires each have a plurality or bundle of conductors 14, 16, respectively, of a biocompatible material, e.g. ten-strand stainless steel. The conductor bundles are surrounded by flexible, biocompatible insulation material 18, 20 e.g. extruded FEP teflon. The multi-strand wires 10, 12 are wound helically or spirally around a biocompatible, polymeric core 22, e.g. a polyprolene suture material. For greater toughness, the single helical portion is encased in a biocompatible sheath 24, e.g. silastic tubing. In order to prevent body fluids from accumulating in the sheath, the ends are sealed with silastic plugs 26. An electrical connector 28 with a stress relief spring is connected to the conductors at one end. Optionally, as shown in FIG. 3, the sheath 24 may be eliminated.

With reference to FIG. 4, to form the open double helix portion B, a length of the single helix lead construction, without the outer sheath, is wrapped into a larger diameter, open core helix. More specifically, the open helix portion B is formed by wrapping the single helix length on a mandrel and heating it for stress relief such that after the mandrel is removed, the open double helix section holds its open helical configuration and functions as an easily elongated spring.

In the electrical connection section C, the insulation 18, 20 is removed from the multi-strand electrical conductors 14, 16. The stripped multi-strand conductors are wrapped around the polyprolene core 22 in interleaved helices to form a single helix deinsulated section. The single helix deinsulated section is further wrapped into a second, open spiral. The polyprolene or other polymeric central core 22 extends from a terminal end of the electrically conductive section to facilitate implantation. A plurality of anchors 32 are mounted at intervals along the deinsulated section. In the illustrated embodiment, each barb is a length of electrical conductor which is mechanically connected to the deinsulated portion. Preferably, the barbs 32 are stainless steel, although other biocompatible electrical conductors are also contemplated.

Alternately, a single wire may be wrapped on the polyprolene core to form the single helix section. The single helix section is then wound into an open spiral to form the open double helix section B.

With reference to FIG. 5, as yet alternate embodiment, the first wire 10 may be wrapped around the polyprolene core 22 in a first layer. The second wire 12 is wrapped peripherally around the first helically wound wire. This two-wire, single helix section is again wrapped into an open, second helix to form the open double helix section B.

Figure 6:
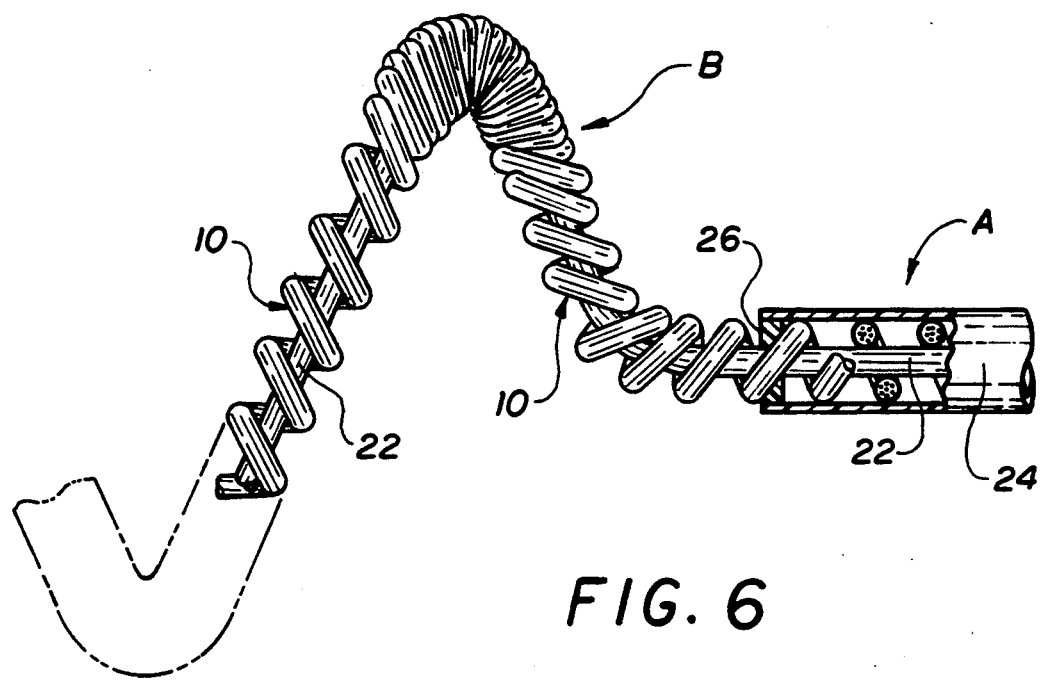
FIG. 6 is a side view in partial section of an alternate embodiment with a single helix lead with sheathing.

With reference to FIG. 6, as yet another embodiment, a single wire 10 is wrapped around the core 22. The single wire, single helix is wrapped into an open double helix.

With reference to FIG. 7A, a probe 50 is inserted through a small incision 52 into a proposed site for implantation. The probe has an insulated cover 54 with the exposed electrical portion 56 at its tip and an electrical connection area 58 at the opposite end. An electrical stimulator is connected with the exposed end 58 to test for muscular response. The position of the tip 56 is selectively adjusted until a desired muscular response is attained. The depth and angular position of the probe are measured and recorded.

With reference to FIG. 7B, a retractor 60 is inserted adjacent the probe to enlarge the incision slightly. A barrel 62 is slid over the probe and through the incision in accordance with the measured depth. The probe is then removed—the inserted portion of the barrel denotes the proposed implantation site.

With reference to FIG. 7C, the exposed end of the polyprolene core 22 is inserted into a bore of a cannula 64 and the double helix exposed portion C and lead portion B are wrapped therearound. The cannula and the electrode are inserted into the barrel 62 in accordance with the previously measured depth.

With reference to FIG. 7D, a tamper 66 is inserted into the barrel 62 to engage a rearmost one of the double helix loops of the lead. The cannula 64 is withdrawn, as is the barrel 62.

With reference to FIG. 7E, the tamper is also withdrawn leaving the single helix portion A of the lead extending from the incision 52 (FIG. 7F). Although a percutaneous interface may be inserted at this point, the end of the single helix lead possibly with a portion of the open double helix lead is more normally channeled below the skin to a preselected location. This enables each or a multiplicity of electrodes to be implanted from an optimally located entrance point, enables all the leads to be collected together at a common location. The common location may be an implanted stimulator, a percutaneous interface, or the like. The incision 52 is given appropriate medical treatment to promote early healing.

With reference to FIGS. 8A, 8B and 8C, the retractor 60 has a generally semi-circular leading edge 70 with an inner diameter 72 which is comparable to the outer diameter of the barrel 62. The retractor curves about 90° away from the side of the semi-circle to provide a guide area 74 that is readily engaged, like a shoehorn, by the barrel 62. The guide portion is interconnected with a handle 76 of appropriate size and shape for convenient surgical utilization.

The invention has been described with reference to a preferred embodiments. Obviously, modifications and alterations will occur to others upon reading and understanding the preceding detailed specification. It is intended that the invention be construed as including all such alterations and modifications insofar as they come within the scope of the appended claims or the equivalents thereof.

Having thus described the preferred embodiments, the invention is now claimed to be:

1. A functional electrical stimulation electrode assembly comprising:
   a first lead portion in which a first insulated electrical conductor is wrapped helically around an elongated, flexible core;
   a second lead portion in which the core with the insulated helically wound conductor is wrapped in an open helix to define an open double helical lead portion;

an electrical connection portion electrically connected with the second lead portion and including an uninsulated electrical conductor portion wrapped helically around the core, the helically wrapped core and uninsulated electrical conductor portion also being formed in an open helix.

2. The assembly as set forth in claim 1 further including a second insulated electrical conductor wrapped helically around the core along the first lead portion and the open double helical lead portion, the second insulated conductor having its insulation removed adjacent the electrical connection portion and the uninsulated electrical conductor portion being wrapped helically around the core in the electrical connection portion.

3. The electrode as set forth in claim 2 further including a plurality of electrically conductive barbs mechanically anchored along the uninsulated electrical conductor portion.

4. The assembly as set forth in claim 2 wherein the first and second insulated electrical conductors are wrapped in interleaved helices of the same diameter around the core.

5. The assembly as set forth in claim 2 wherein the first insulated conductor is wrapped in a first helix around the core and the second insulated conductor is wrapped in a second helix around tile first insulated conductor.

6. The assembly as set forth in claim 1 further including a plurality of barbs mechanically connected with the uninsulated electrical conductor portion.

7. The assembly as set forth in claim 6 wherein the core extends beyond a terminal end of the electrical connection portion to facilitate insertion within a bore of a cannula during insertion of the electrode assembly.

8. The assembly as set forth in claim 6 wherein the barbs include a plurality of metal barbs mechanically anchored at intervals over an entire length of the uninsulated electrical conductor portion.

9. The assembly as set forth in claim 6 further including a polymeric sheath over the first lead portion and a polymeric sealant sealing at least an end of the polymeric sheath adjacent the second lead portion in a fluid tight seal to prevent body fluids from becoming trapped within the sheath.

10. The assembly as set forth in claim 1 further including a polymeric sheath over the first lead portion and a polymeric sealant sealing at least an end of the polymeric sheath adjacent the second lead portion in a fluid tight seal to prevent body fluids from becoming trapped within the sheath.

11. The assembly as set forth in claim 10 further including a second polymeric seal adjacent a second end of the polymeric sheath to provide a fluid tight seal between the second end of the polymeric sheath and the first lead portion.

12. The assembly as set forth in claim 10 further including a second insulated electrical conductor wrapped helically around the core along the first lead portion and the second lead portion, the second conductor having an uninsulated portion wrapped helically around the electrical connection portion.

13. The assembly as set forth in claim 12 further including a plurality of barbs mechanically connected with the uninsulated electrical conductor portion.

14. An electrode assembly for implantation in skeletal muscles, the assembly comprising:

first and second wires each having a multistrand biocompatible electrical conductor coated with insulation, the first and second wires being wrapped spirally around a polymeric core;

a polymeric sheath covering the first and second wire wrapped core along a first portion;

a second portion of the first and second wire wrapped core being formed into an open spiral;

terminal portions of the first and second wires being uninsulated, the multistrand electrical conductors being wrapped around the polymeric core and the multistrand conductor wrapped core being formed in an open spiral;

barbs connected with the multistrand electrical conductor wrapped core open spiral for anchoring to skeletal muscle.

* * * * *

UNITED STATES PATENT AND TRADEMARK OFFICE
CERTIFICATE OF CORRECTION

PATENT NO. : 5,366,493
DATED : November 22, 1994
INVENTOR(S) : Scheiner, et al.

It is certified that error appears in the above-indentified patent and that said Letters Patent is hereby corrected as shown below:

Column 5, line 29, claim 5,
    delete --tile-- and substitute the word "the."

Signed and Sealed this

Twenty-seventh Day of June, 1995

Attest:

BRUCE LEHMAN

*Attesting Officer*    *Commissioner of Patents and Trademarks*